(12) United States Patent
Polonsky et al.

(10) Patent No.: US 8,003,319 B2
(45) Date of Patent: Aug. 23, 2011

(54) SYSTEMS AND METHODS FOR CONTROLLING POSITION OF CHARGED POLYMER INSIDE NANOPORE

(75) Inventors: Stanislav Polonsky, Putnam Valley, NY (US); Stephen M. Rossnagel, Pleasantville, NY (US); Gustavo A. Stolovitzky, Riverdale, NY (US)

(73) Assignee: International Business Machines Corporation, Armonk, NY (US)

( * ) Notice: Subject to any disclaimer, the term of this patent is extended or adjusted under 35 U.S.C. 154(b) by 348 days.

(21) Appl. No.: 11/670,621

(22) Filed: Feb. 2, 2007

(65) Prior Publication Data

US 2008/0187915 A1    Aug. 7, 2008

(51) Int. Cl.
- C12Q 1/68 (2006.01)
- G01N 33/53 (2006.01)
- C12M 1/00 (2006.01)
- C12M 1/34 (2006.01)
- C12M 3/00 (2006.01)

(52) U.S. Cl. ....... 435/6; 435/7.1; 435/283.1; 435/287.2; 204/403.01; 204/600; 977/924

(58) Field of Classification Search ............... 435/6, 7.1, 435/283.1, 287.2; 977/924
See application file for complete search history.

(56) References Cited

U.S. PATENT DOCUMENTS

| | | | |
|---|---|---|---|
| 5,795,782 A | 8/1998 | Church et al. | |
| 6,627,067 B1 | 9/2003 | Branton et al. | |
| 7,279,337 B2 * | 10/2007 | Zhu | 436/43 |
| 7,468,271 B2 * | 12/2008 | Golovchenko et al. | 435/287.2 |
| 2003/0141189 A1 * | 7/2003 | Lee et al. | 204/600 |
| 2004/0011650 A1 * | 1/2004 | Zenhausern et al. | 204/547 |
| 2006/0019259 A1 | 1/2006 | Joyce | |
| 2006/0057585 A1 | 3/2006 | McAllister | |
| 2006/0063171 A1 | 3/2006 | Akeson et al. | |
| 2006/0068401 A1 * | 3/2006 | Flory et al. | 435/6 |

FOREIGN PATENT DOCUMENTS

| | | |
|---|---|---|
| WO | WO0036407 | 6/2000 |
| WO | WO0181896 | 11/2001 |
| WO | WO2006/027780 | * 3/2006 |
| WO | PCTEP08050562 | 5/2008 |

OTHER PUBLICATIONS

D. Fologea et al., "Slowing DNA Translocation in a Solid-State Nanopore," American Chemical Society, Nano Letters, 2005, pp. 1734-1737, vol. 5, No. 9.
J. Lagerqvist et al., "Fast DNA Sequencing via Transverse Electronic Transport," American Chemical Society, Nano Letters, 2006, pp. 779-782, vol. 6, No. 4.
J. Li et al., "Ion-Beam Sculpting at Nanometre Length Scales," Macmillan Magazines Ltd., Nature, Jul. 2001, pp. 166-169, vol. 412.
A.J. Storm et al., "Translocation of Double-Strand DNA Through a Silicon Oxide Nanopore," The American Physical Society, Physical Review, 2005, pp. 1-10, E71.

* cited by examiner

Primary Examiner — Stephen Kapushoc
Assistant Examiner — Narayan Bhat
(74) Attorney, Agent, or Firm — Ryan, Mason & Lewis, LLP (57) ABSTRACT

Techniques for controlling the position of a charged polymer inside a nanopore are provided. For example, one technique includes using electrostatic control to position a linear charged polymer inside a nanopore, and creating an electrostatic potential well inside the nanopore, wherein the electrostatic potential well controls a position of the linear charged polymer inside the nanopore.

20 Claims, 5 Drawing Sheets

SYSTEMS AND METHODS FOR CONTROLLING POSITION OF CHARGED POLYMER INSIDE NANOPORE

FIELD OF THE INVENTION

The present invention relates to polymer characterization and, more particularly, to systems and methods for controlling the position of a charged polymer inside a nanopore.

BACKGROUND OF THE INVENTION

Rapid, reliable, and inexpensive characterization of polymers, particularly the sequencing of nucleic acids, has become increasingly important. One potential application of polymer characterization is in the field of personalized medicine. For example, potential benefits of polymer characterization may include treatment of disease by identifying patients who will gain the greatest benefit from a particular medicine, and those who are most at risk of adverse reactions. The ability to read individual genomes quickly and economically would be a beneficial tool in the development of personalized medicine.

Existing approaches have attempted to address the need for rapid, reliable and inexpensive polymer characterization. For example, some existing approaches use sequencing by synthesis, which includes detection of optical signals during synthesis of complementary deoxyribonucleic acid (DNA) strands. However, sequencing by synthesis produces problems such as, for example, slow reagent cycling times (tens of seconds), short read lengths (tens to hundreds of bases) and expensive reagents. Slow reagent cycling times is a fundamental problem because it results in a need to change chemistry in a flow cell to remove fluorophore from each incorporated base.

Also, other exiting approaches use nanopore sequencing, which includes driving DNA through a nanopore and measuring the electrical current in the DNA as a function of the nucleotides inside the nanopore. Some existing approaches attempt to thread a long DNA molecule through a few nanometer-wide nanopore and use physical differences between the four base types to read the sequence of bases in DNA The price of nanopore sequencing is expected to be very low since the method needs neither expensive chemical reagents nor expensive optical readout. However, single nucleotide resolution has not yet been achieved. Existing approaches using nanopore sequencing cannot resolve a single base, but, rather, require at least a few dozen bases.

Some existing approaches rely on using a readily available-in-nature biological nanopore, that is, α-hemolysin channel (for example, U.S. Pat. No. 5,795,782 entitled "Characterization of individual polymer molecules based on monomer-interface interactions."). Some existing approaches detect events of DNA translocation through a nanopore by measuring sub-millisecond blockades of ionic current through the nanopore but fail to resolve single bases within the translocated molecule. Despite the ease of obtaining biological nanopores, the difficulties of dealing with unreliable and poorly understood membrane proteins lead many researches to use solid-state nanopores.

Other existing approaches use nanopores with diameters of between two and three nanometers (nm), fabricated by using such materials as $Si_3N_4$ or $SiO_2$ (for example, U.S. Pat. No. 6,627,067 entitled "Molecular and atomic scale evaluation of biopolymers," and U.S. Patent Application No. 2006/0063171 entitled "Methods and apparatus for characterizing polynucleotides."). Solid-state nanopores also provide the possibility of placing metal electrodes in the vicinity of probed DNA. This arrangement, in theory, allows researchers to measure the tunnel current through a single base, and, consequentially, potentially discriminate the bases of different types. In existing approaches, however, repetitive measurements of tunnel current are necessary to provide enough statistics to determine the base type with a high degree of accuracy.

Existing approaches in the area of mechanical polymer characterization include U.S. Patent Application No. 2006/0057585 entitled "Nanostepper/Sensor Systems and Methods of Use Thereof," filed Sep. 10, 2004. This approach includes a nanopore system and a first nanostepper system, wherein the nanopore system includes a structure having a nanopore aperture, and the first nanostepper system includes an x-/y-direction moving structure and a first nanostepper arm positioned adjacent the structure.

At present, nanopore sequencing is still theoretical, as single nucleotide resolution has not yet been achieved. One of the possible reasons for such unsuccessful experimental results in existing approaches is that the translocation of DNA through the nanopore is too fast and erratic for current measurement methods to reliably resolve the type of a single nucleotide. Despite attempts to slow down the translocation speed by optimization of various parameters (for example, electrolyte temperature, salt concentration, viscosity, and the electrical bias voltage across the nanopore), existing approaches have still been unsuccessful in attaining single nucleotide resolution.

It would thus be desirable to overcome these and other limitations in existing polymer characterization approaches.

SUMMARY OF THE INVENTION

Principles of the present invention provide techniques for controlling the position of a charged polymer inside a nanopore.

For example, in one aspect of the invention, a technique for controlling the position of a linear charged polymer inside a nanopore includes the following steps. Electrostatic control is used to position a linear charged polymer inside a nanopore. Also, an electrostatic potential well is created inside the nanopore, wherein the electrostatic potential well controls a position of the linear charged polymer inside the nanopore.

In another aspect of the invention, a technique for characterizing a linear charged polymer includes the following steps. A time-dependent voltage is applied to each of two or more drag electrodes to attract a linear charged polymer from a part of a reservoir preceding a nanopore (that is, a CIS part) to a part of a reservoir following the nanopore (that is, a TRANS part). Entry of the linear charged polymer inside the nanopore is detected. The time-dependent voltages are reduced or removed from the two or more drag electrodes. A time-dependent voltage is applied to each of one or more locking electrodes to create an electrostatic potential well, wherein the electrostatic potential well controls a position of the linear charged polymer. One or more characterization activities are performed on one or more monomers of the linear charged polymer. The time-dependent voltage is reduced from each of the locking electrodes and the electrostatic potential well. Also, the time-dependent voltages are increased or reapplied to each drag electrode to translocate the linear charge polymer by one or more monomers.

In another aspect of the invention, an apparatus for controlling the position of a linear charged polymer inside a nanopore includes the following components. A reservoir is included that is separated by a membrane into two parts (that is, the CIS part and the TRANS part), wherein the membrane is formed as a stack of one or more locking electrodes. A nanopore is included in the membrane, wherein the nanopore connects the two parts of the reservoir. A drag electrode is in each part of the reservoir. Also, the apparatus includes a control unit, wherein the control unit outputs time-dependent voltages to each drag electrode and each locking electrode.

In contrast to the above-mentioned limitations in existing approaches, principles of the invention overcome such shortcomings by, for example, controlling the position of a polymer (for examples DNA) inside a nanopore with single monomer (for example, nucleotide) accuracy.

These and other objects, features and advantages of the present invention will become apparent from the following detailed description of illustrative embodiments thereof which is to be read in connection with the accompanying drawings.

DETAILED DESCRIPTION OF PREFERRED EMBODIMENTS

As noted above, it would be beneficial to not only slow down the translocation of charged polymers, but to control the position of a polymer inside a nanopore with single nucleotide accuracy. Principles of the present invention use an electrostatic potential well to lock the positions of linear polymers carrying localized charges along their chain. Electrostatic control (ESC) is used to position and move a polymer such as, for example, deoxyribonucleic acid (DNA), inside a nanopore.

Principles of the present invention apply varying voltages to metal layers in order to produce sensitive control of the position of negatively-charged nucleotides. The control may be similar to the charge control in charge-coupled device (CDD) sensors.

One or more embodiments of the present invention detect nucleotide type by measuring tunnel current of capacitance change between layers. Also, layer voltages may be modulated with high frequency signals in order to utilize lock-in measurement techniques.

Principles of the present invention are applicable to all linear polymers carrying localized charges along their chain. For example, such polymers may include DNA in solution, which is a charged polymer, carrying negative electrical charges on phosphate groups in the double helix of the molecule.

Given the above realizations made in accordance with one or more embodiments of the present invention, and general features associated therewith, the remainder of the detailed description will provide an illustrative explanation of techniques for implementing such realizations and features in the context of FIGS. 1 through 5.

Figure 1:
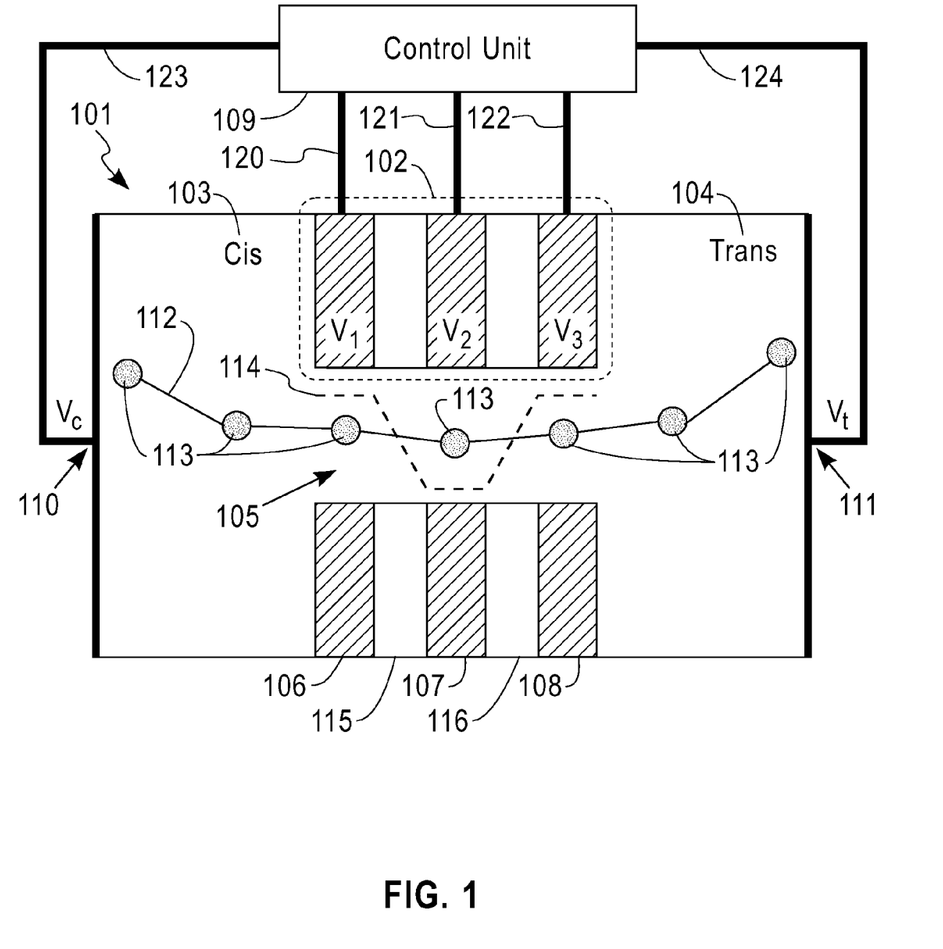
FIG. 1 is a diagram illustrating a cross-section of an exemplary polymer position control device, according to an embodiment of the present invention.

FIG. 1 is a diagram illustrating a cross-section of an exemplary polymer position control device, according to an embodiment of the present invention. By way of illustration, FIG. 1 depicts an apparatus for controlling the position of a linear charged polymer inside a nanopore including a reservoir 101 that is divided by a membrane 102 into two parts, the CIS part 103 (preceding the nanopore) and the TRANS part 104 (following the nanopore). A membrane 102 is formed as a stack of one or more electrodes 106, 107, 108 separated by insulators 115 and 116. The electrical potential of each electrode ($V_1$, $V_2$, $V_3$) is set independently by control unit 109. Electrodes 106, 107, and 108 are referred to as locking electrodes. $V_1$, $V_2$, $V_3$ are the respective voltages for electrodes 106, 107, 108. Also, the voltages connect to the locking electrodes via wires 120, 121 and 122, respectively. The stack of locking electrodes can include a first locking electrode and a second locking electrode separated by one or more insulators.

CIS 103 and TRANS 104 parts are connected by a nanopore 105 in the membrane 102. Locking electrodes (for example, 106, 107, 108) are capable of creating the electrostatic potential well 114 inside the nanopore by, for example, creating a potential difference between the electrodes. As way of example, electrode 106 may receive a voltage of 0 volts, electrode 107 may receive a voltage of 1 volts, and electrode 108 may receive a voltage of 0 volts, resulting in the creation of a potential well.

Control unit 109 provides bias Cis voltage ($V_c$) to electrode 110 in the CIS part 103 via wire 123, and also provides Trans voltage ($V_t$) to electrode 111 in the TRANS part of the reservoir 104 via wire 124. Electrodes 110 and 111 are referred to as drag electrodes. It is to be appreciated, however, that other embodiments of the present invention may include two or more drag electrodes.

Linear polymer 112 with localized charges 113 may be, for example, originally located in the CIS part 103. The voltage difference $V_t$-$V_c$ (drag voltage) attracts the polymer from CIS 103 to the TRANS part 104. Control unit 109 detects the entrance of polymer inside the nanopore 105. The detection can be accomplished, for example, by measuring the variation of ion current between drag electrodes 110 and 111, or locking electrodes 106, 107 and 108. In a preferred embodiment, the measurement is made between drage electrode 110 and drag electrode 111. It is to be appreciated, however, that measurements can also made using any combination of locking and drag electrodes.

Once the polymer is inside the nanopore 105, the drag voltage is reduced or removed and voltages are applied to locking electrodes (for example, 106, 107 and 108) to create a potential well 114.

Figure 3:
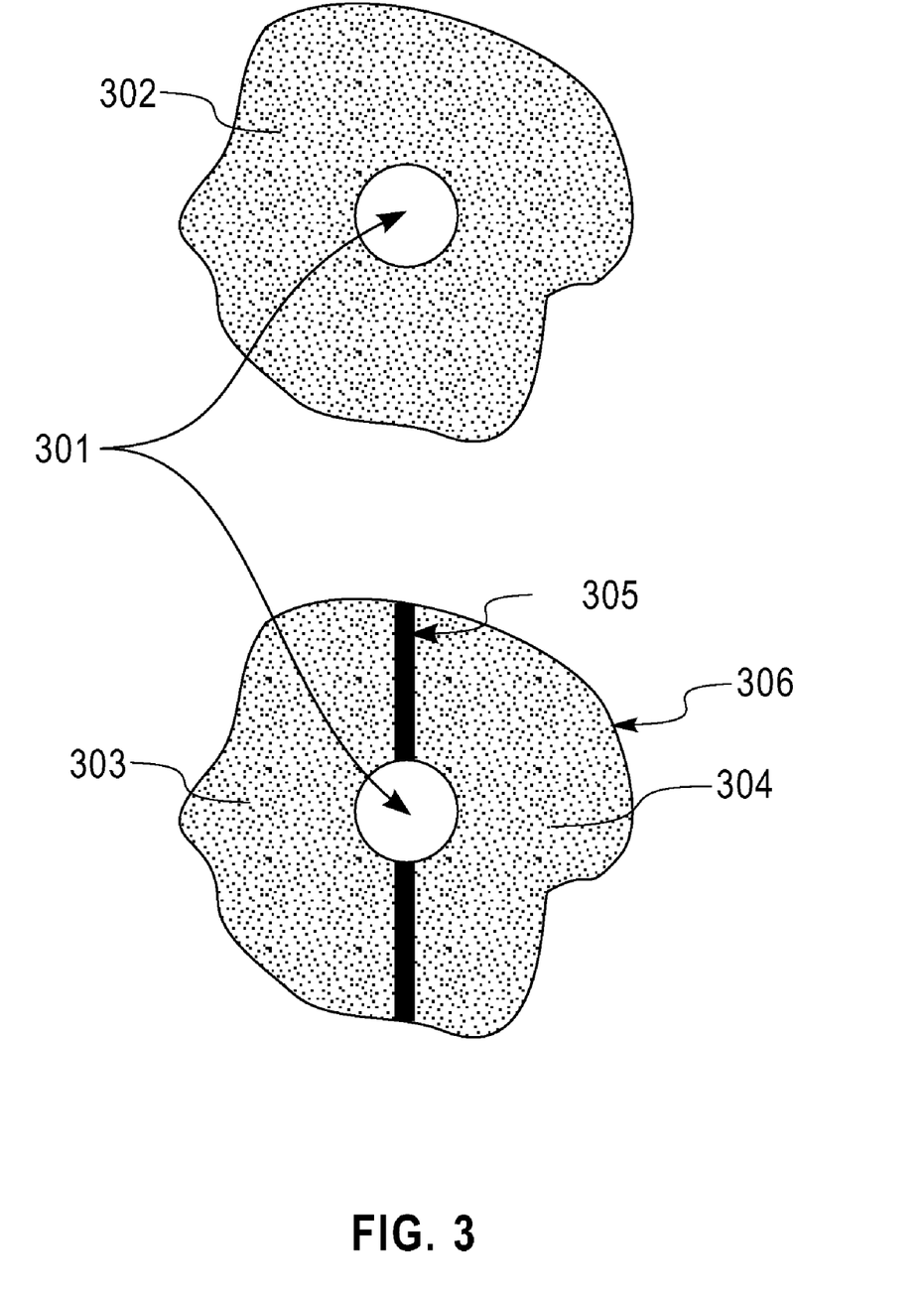
FIG. 3 is a diagram illustrating exemplary locking electrode geometries, according to an embodiment of the present invention.

The drag electrodes and locking electrodes can be controlled independently, or can be connected in parallel. In addition, the locking and drag electrodes may be made or created from any conductive material (for example, gold, carbon, etc.). Also, the locking electrodes may have one or more geometries, as illustrated by FIG. 3 below.

In one or more embodiments of the present invention, the above apparatus can be used to sequence polymers such as, for example, DNA, ribonucleic acid (RNA), protein molecules and other charged polymers, as well as in processes such as, for example, chemical modification of polymers.

Principles of the present invention may also be used to count the number of polymers with a given characteristic that are present in the solution originally in the CIS reservoir, such as would be needed to measure the number of RNA transcripts in cellular extract. One or more embodiments of the present invention may also be used to separate polymers with one or more specific characteristics from the solution on the CIS part to the solution on the TRANS part.

In a preferred embodiment, three locking electrodes are used. It is to be appreciated, however, that one or more locking electrodes may be used in other embodiments. In an embodiment wherein one locking electrode is used, a potential well is created as a result of the voltage of the locking electrode. For example, a locking electrode with a voltage of 1 volt may create a potential well in a surrounding environment of lower or neutral voltage. In FIG. 1, locking electrodes 106, 107 and 108 are shown to have cylindrical geometry (for example, metal plain with a hole). In other embodiments of the present invention, however, the geometry of the locking electrodes and drag electrodes can vary. By way of example, an illustrative embodiment may include two electrodes per layer, each occupying a half plain with a hole in the center. As illustrated in FIG. 3 below, a hole is representative of a nanopore, a layer represents electrodes without a hole, and a half plain represents a geometry that has been divided into two sections.

A potential well can have one or more spatially dependent profiles. As way of example, FIG. 1 depicts a potential well 114 having a trapezoidal spatially dependent profile. In a preferred embodiment, one nanopore is used. It is to be appreciated, however, that one or more nanopores can be used in other embodiments wherein, for example, more than one polymer is being positionally controlled and/or more than one portion of a polymer is being positionally controlled.

A preferred embodiment of the present invention includes a control unit. It is to be appreciated, however, that other embodiments may include one or more control units. A control unit may include, for example, a computer that connects to a specialized board with an application-specific integrated circuit (ASIC), wherein the board connects to the device. A control unit may also, for example, be integrated with the device by way of a Nano-Electro-Mechanical System (NEMS), wherein a nanofluidics part (for example, a reservoir with DNA) can be combined with electronics (for example, a control unit). A control unit implements the step of applying time-dependent voltages to the drag electrodes to attract a linear charged polymer from a CIS part of a reservoir to a TRANS part of a reservoir, as well as the step of applying a time-dependent voltage to each locking electrode to create an electrostatic potential well, wherein the electrostatic potential well controls the position of the linear charged polymer.

Moreover, in an illustrative embodiment of the present invention, the control unit implements the steps of detecting entry of the linear charged polymer inside the nanopore, and reducing the time-dependent voltages from the drag electrodes.

A control unit may also implement the steps of performing one or more characterization activities on a monomer of the linear charged polymer, reducing the time-dependent voltage from each locking electrode and the electrostatic potential well, and increasing or re-applying the time-dependent voltages to the drag electrodes to translocate the linear charge polymer by one or more monomers.

Also, in one or more embodiments of the present invention, the control unit may implement repetition of one or more actions. Such actions may include, for example, reducing or removing the time-dependent voltages from the drag electrodes, and increasing or re-applying the time-dependent voltage to each locking electrode to create an electrostatic potential well. Such repeated actions may also include, for example, performing one or more characterization activities on a monomer of the linear charged polymer, reducing or removing the time-dependent voltage from each locking electrode and the electrostatic potential well, and increasing or re-applying the time-dependent voltages to the drag electrodes to translocate the linear charge polymer by one or more monomers.

In an illustrative embodiment of the invention, the control unit implements repetition of the above steps for an entire polymer.

Figure 2:
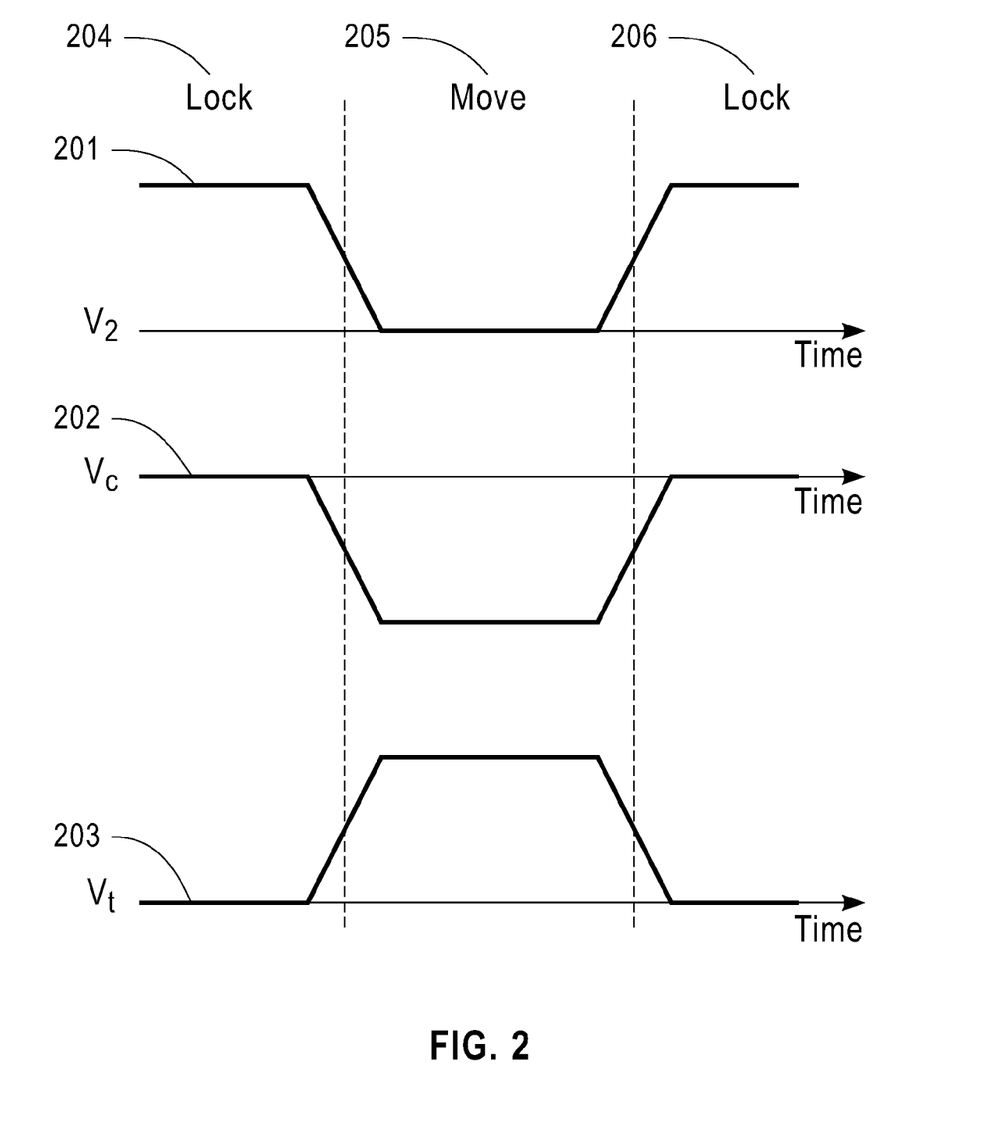
FIG. 2 is a diagram illustrating exemplary applications of time-dependent voltages, according to an embodiment of the present invention.

FIG. 2 is a diagram illustrating exemplary applications of time-dependent voltages, according to an embodiment of the present invention. By way of illustration, FIG. 2 depicts three positions, a lock position 204, a move position 205 and a lock position 206. Moving a potential wave drags the one or more trapped charges, and stopping the wave localizes the one or more charges. FIG. 2 also depicts application of time-depiction voltages to three separate electrodes.

As illustrated in FIG. 1, a preferred embodiment of the present invention includes two drag electrodes ($V_c$ 110 and $V_t$ 111) and three locking electrodes (106, 107 and 108) with corresponding electrical potential ($V_1$, $V_2$ and $V_3$, respectively). In FIG. 2, exemplary application of time-dependent voltages are depicted for each drag electrode (202 and 203) as well as for the second or middle locking electrode (201). As way of example only, application of time-dependent voltages may proceed as follows. In 201, the voltage application ($V_2$) for the second or middle locking electrode (for example, 107) may include 1 volt in lock position 204, 0 volts in move position 205, and 1 volt in lock position 206 (the first and third locking electrodes, for example, 106 and 108, would have voltage levels that remain constant). In 202, the voltage application ($V_c$) for drag electrode 110 may include 0 volts in lock position 204, −1 volt in move position 205, and 0 volts in lock position 206. In 203, the voltage application ($V_t$) for drag electrode 111 may include 0 volts in lock position 204, 1 volt in move position 205, and 0 volts in lock position 206.

FIG. 3 is a diagram illustrating exemplary locking electrode geometries, according to an embodiment of the present invention. By way of illustration, FIG. 3 depicts two exemplary locking electrode geometries, namely, a cylindrical geometry 302 and a half plain geometry 306, both of which include a nanopore 301. Also, the exemplary half plain geometry 306 includes an insulator 305 separating independently-controlled locking electrodes 303 and 304.

Figure 4:
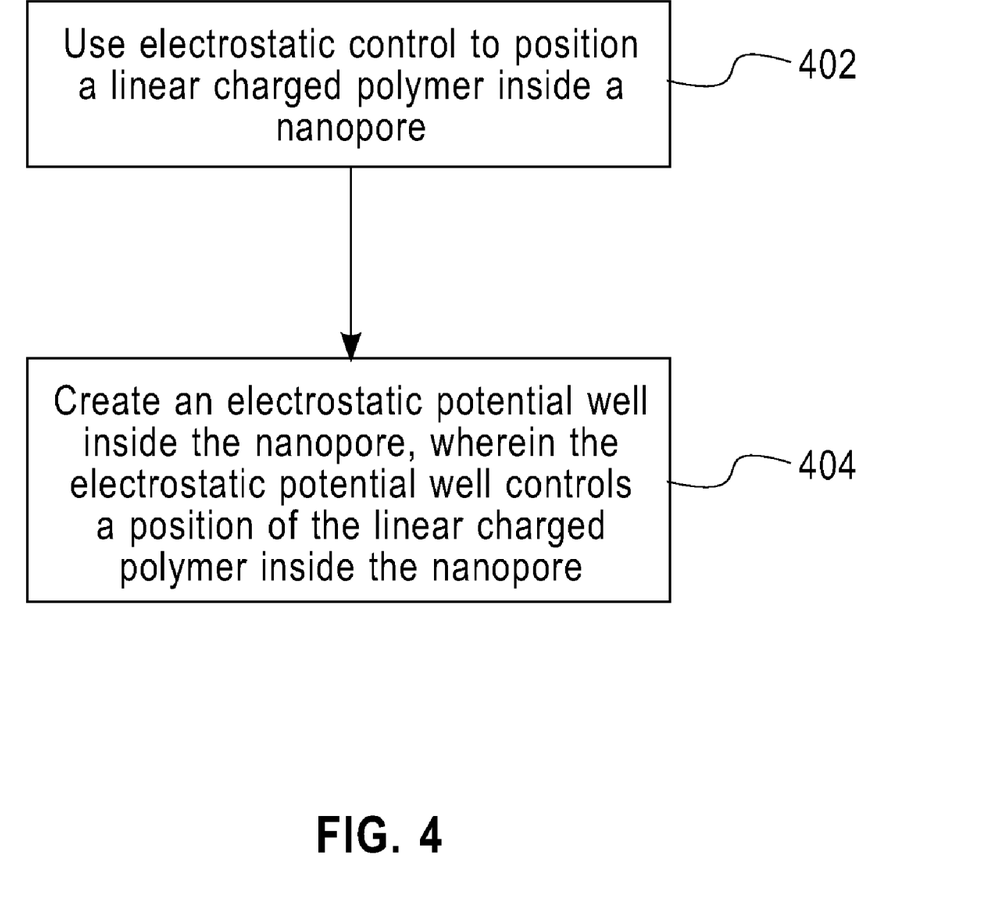
FIG. 4 is a flow diagram illustrating techniques for controlling the position of a linear charged polymer inside a nanopore, according to an embodiment of the present invention.

FIG. 4 is a flow diagram illustrating techniques for controlling the position of a linear charged polymer inside a nanopore, according to an embodiment of the present invention. Step 402 includes using electrostatic control to position a linear charged polymer inside a nanopore. Step 404 includes creating an electrostatic potential well inside the nanopore, wherein the electrostatic potential well controls a position of the linear charged polymer inside the nanopore. The linear charged polymer may include, for example, DNA, RNA and/or one or more protein molecules.

One or more embodiments of the present invention may also include the step of detecting entry of the linear charged polymer inside the nanopore. Detecting entry of the linear charged polymer may include measuring a variation of ion current between the drag electrodes.

Figure 5:
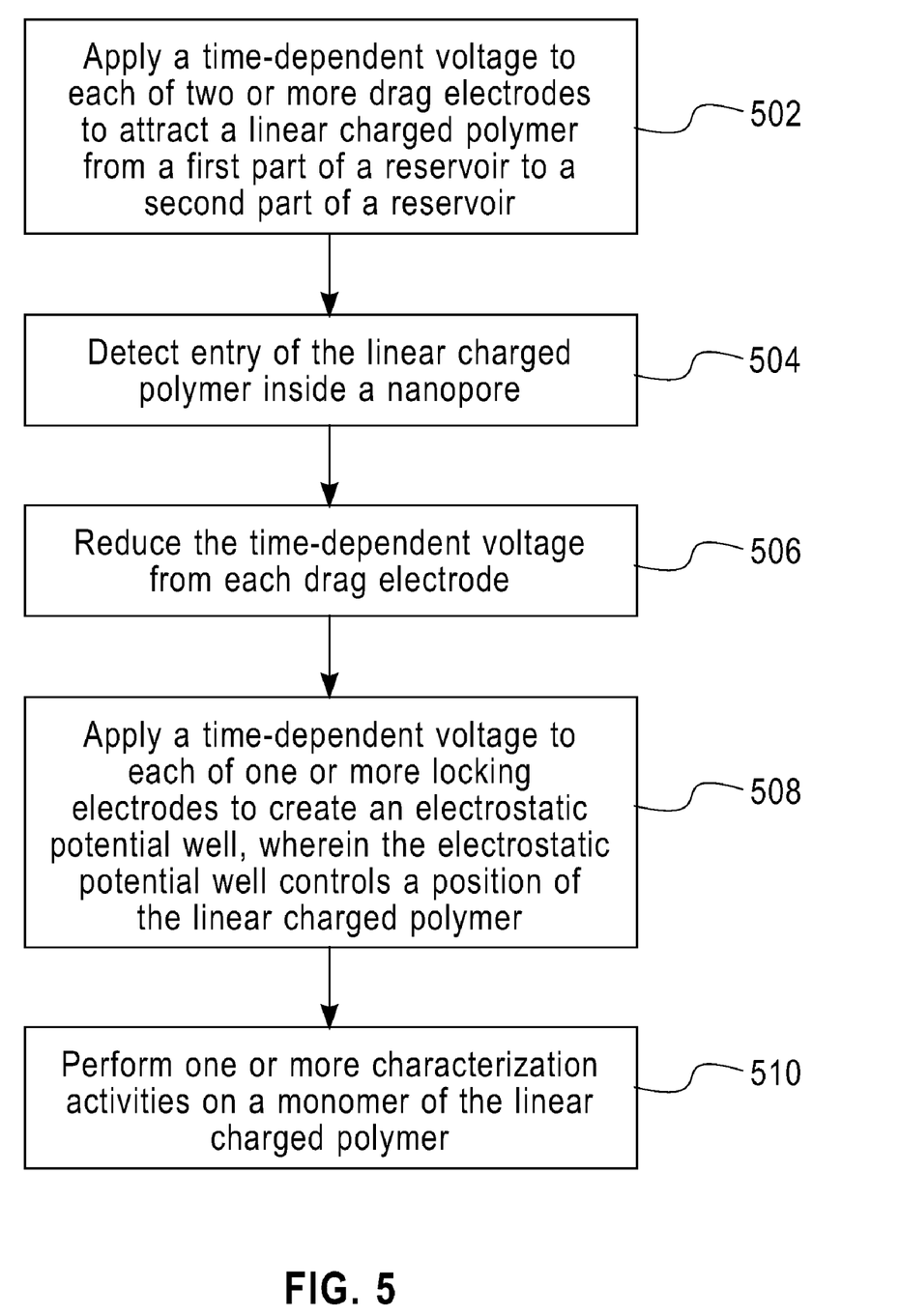
FIG. 5 is a flow diagram illustrating techniques for characterizing a linear charged polymer, according to an embodiment of the present invention.

FIG. 5 is a flow diagram illustrating techniques for characterizing a linear charged polymer, according to an embodiment of the present invention. Step 502 includes applying a time-dependent voltage to each of two or more drag electrodes to attract a linear charged polymer from a first part of a reservoir to a second part of a reservoir. The first part of the reservoir may include a CIS part and the second part of the reservoir may include a TRANS part. Step 504 includes detecting entry of the linear charged polymer inside a nanopore. Step 506 includes reducing the time-dependent voltage from each drag electrode. Step 508 includes applying a time-dependent voltage to each of one or more locking electrodes to create an electrostatic potential well, wherein the electrostatic potential well controls a position of the linear charged polymer. Step 510 includes performing one or more characterization activities on a monomer of the linear charged polymer. An illustrative embodiment of the invention may also include the step of reducing the time-dependent voltage from each locking electrode and the electrostatic potential well, as well as the step of increasing the time-dependent voltage to each drag electrode to translocate the linear charged polymer by one or more monomers.

One or more embodiments of the present invention may also include repetition of one or more steps. Steps to be considered for repetition may include, for example, reducing or removing the time-dependent voltage from each drag electrode, and applying a time-dependent voltage to each locking electrode to create an electrostatic potential well. Steps to be considered for repetition may also include, for example, performing one or more characterization activities on a monomer of the linear charged polymer, reducing or removing the time-dependent voltage from each locking electrode and the electrostatic potential well, and increasing the time-dependent voltage to each drag electrode to translocate the linear charge polymer by one or more monomers. Also, in an illustrative embodiment of the present invention, the above-mentioned steps are repeated for an entire polymer.

Characterization activities may include, for example, DNA sequencing, counting the number of polymers with a given characteristic that are present in a solution originally in the CIS part of a reservoir, counting the number of monomers in each polymer, as well as separating two or more polymers according to one or more characteristics. Other characterization activities may include chemical modification of the linear charged polymer may occur, as well as measuring tunnel current between a first locking electrode and a second locking electrode, and measuring capacitance change between a first locking electrode and a second locking electrode.

The step of increasing the time-dependent voltage to each drag electrode may include re-applying each time-dependent voltage. Also, increasing the time-dependent voltage to each drag electrodes may be performed for the duration of a selected time interval, wherein the time interval is sufficient to translocate each polymer by one monomer. A linear charged polymer may be translocated in both directions.

The step of reducing the time-dependent voltage from each drag electrode may include removing each time-dependent voltage completely.

In a preferred embodiment of the invention, an exemplary technique for characterizing a linear charged polymers may occur as follows. A linear polymer with localized charges may be, for example, originally located in the CIS part of the reservoir. The voltage difference of $V_t$-$V_c$ (drag voltage) attracts the polymer from CIS part to the TRANS part of the reservoir. A control unit detects the entrance of the polymer inside the nanopore, wherein the detection can be accomplished, for example, by measuring the variation of ion current between drag electrodes or locking electrodes.

Once the polymer is inside the nanopore, the drag voltage is reduced or removed and a voltage is applied to each locking electrode to create an electrostatic potential well. The depth of a potential well can be, for example, sufficient to lock at least one point charge or monomer. After the polymer is locked, measurements of the monomer contained in the potential well are initiated.

Also, the potential well can be removed, and the drag voltage can be increased or re-applied for a time interval T. The value of T is selected on a basis that would translocate the polymer by a certain required distance such as, for example, the distance between localized charges. In a preferred embodiment of the present invention, this distance corresponds to the length of a single monomer.

By changing the polarity of drag voltage, it is possible to translocate the polymer in both directions. Translocation of a polymer may be executed in both directions in order to double-check the measured DNA sequence.

In an illustrative embodiment of the invention, the above-described steps are repeated until the polymer completely translocates from the CIS part of the reservoir to the TRANS part of the reservoir and leaves the nanopore. The sequence of drag and locking voltage application illustrated in FIG. 5 is an exemplary embodiment of the invention. It is to be appreciated that the sequence of drag and locking voltage application can vary.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for controlling a position of a linear charged polymer inside a nanopore, comprising the steps of:
    using electrostatic control to position a linear charged polymer inside a nanopore; and
    applying an independent voltage to each of three locking electrodes, wherein the three locking electrodes each have a cylindrical geometry and are separated by one or more insulators, creating an electrostatic potential well inside the nanopore that varies along nanopore via setting an electrical potential of each of the three locking electrodes independently, wherein the electrical potential of a second locking electrode differs from the electrical potential of a first and third locking electrode, and wherein the electrostatic potential well controls a position of the linear charged polymer inside the nanopore, wherein controlling a position of the linear charged polymer inside the nanopore comprises using the electrostatic potential well to lock the position of one monomer of the linear charged polymer inside the nanopore.

2. The method of claim 1, wherein the step of using electrostatic control to position a linear charged polymer inside a nanopore comprises detecting entry of the linear charged polymer inside the nanopore.

3. The method of claim 2, wherein the step of detecting entry of the linear charged polymer comprises measuring a variation of ion current between two or more electrodes used in controlling a position of a linear charged polymer inside a nanopore.

4. The method of claim 1, wherein the linear charged polymer comprises one of deoxyribonucleic acid (DNA), ribonucleic acid (RNA) and a protein molecule.

5. A method for characterizing a linear charged polymer, comprising the steps of:
    applying a time-dependent voltage to each of two or more drag electrodes to attract a linear charged polymer from a first part of a reservoir to a second part of a reservoir;
    detecting entry of the linear charged polymer inside a nanopore;

reducing the time-dependent voltage from each drag electrode;

applying an independent time-dependent voltage to each of three locking electrodes, wherein the three locking electrodes each have a cylindrical geometry and are separated by one or more insulators, creating an electrostatic potential well inside the nanopore that varies along the nanopore via setting an electrical potential of each of the three locking electrodes independently, wherein the electrical potential of a second locking electrode differs from the electrical potential of a first and third locking electrode, and wherein the electrostatic potential well controls a position of the linear charged polymer, and wherein controlling a position of the linear charged polymer inside the nanopore comprises using the electrostatic potential well to lock the position of one monomer of the linear charged polymer inside the nanopore; and performing one or more characterization activities on a monomer of the linear charged polymer.

6. The method of claim 5, wherein the linear charged polymer comprises DNA, and wherein performing one or more characterization activities comprises DNA sequencing.

7. The method of claim 5, further comprising the steps of reducing the time-dependent voltage from each of the three locking electrodes and the electrostatic potential well; and increasing the time-dependent voltage to each the two or more drag electrodes to translocate the linear charged polymer by one or more monomers.

8. The method of claim 7, further comprising the step of repeating the steps of:

reducing the time-dependent voltage from each of the two or more drag electrodes;

increasing the time-dependent voltage to each of the three locking electrodes to create an electrostatic potential well, wherein the electrostatic potential well controls a position of the linear charged polymer;

performing one or more characterization activities on a monomer of the linear charged polymers;

reducing the time-dependent voltage from each of the three locking electrodes and the electrostatic potential well; and increasing the time-dependent voltage to each of the two or more drag electrodes to translocate the linear charged polymer by one or more monomers.

9. The method of claim 8, wherein the steps are repeated for the entire linear charged polymer.

10. The method of claim 5, wherein the linear charged polymer comprises deoxyribonucleic acid (DNA).

11. The method of claim 5, wherein the linear charged polymer comprises ribonucleic acid (RNA).

12. The method of claim 5, wherein the linear charged polymer comprises a protein molecule.

13. The method of claim 7, wherein one or more characterization activities comprise counting a number of polymers with a given characteristic that are present in a solution, wherein the characterization activity comprising counting a number of polymers with a given characteristic occurs after the step of applying an independent time-dependent voltage to each of the three locking electrodes, creating an electrostatic potential well inside the nanopore, and before the steps of reducing the time-dependent voltage from each of the three locking electrodes and the electrostatic potential well and increasing the time-dependent voltage to each the two or more drag electrodes to translocate the linear charged polymer by one or more monomers.

14. The method of claim 7, wherein one or more characterization activities comprise counting a number of monomers in each polymer, wherein the characterization activity comprising counting a number of monomers in each polymer occurs after the step of applying an independent time-dependent voltage to each of the three locking electrodes, creating an electrostatic potential well inside the nanopore, and before the steps of reducing the time-dependent voltage from each of the three locking electrodes and the electrostatic potential well and increasing the time-dependent voltage to each the two or more drag electrodes to translocate the linear charged polymer by one or more monomers.

15. The method of claim 7, wherein one or more characterization activities comprise chemical modification of the linear charged polymer, wherein the characterization activity comprising chemical modification of the linear charged polymer occurs after the step of applying an independent time-dependent voltage to each of the three locking electrodes, creating an electrostatic potential well inside the nanopore, and before the steps of reducing the time-dependent voltage from each of the three locking electrodes and the electrostatic potential well and increasing the time-dependent voltage to each the two or more drag electrodes to translocate the linear charged polymer by one or more monomers.

16. The method of claim 7, wherein one or more characterization activities comprise separating two or more polymers according to one or more characteristics, wherein the characterization activity comprising separating two or more polymers according to one or more characteristics occurs after the step of applying an independent time-dependent voltage to each of the three locking electrodes, creating an electrostatic potential well inside the nanopore, and before the steps of reducing the time-dependent voltage from each of the three locking electrodes and the electrostatic potential well and increasing the time-dependent voltage to each the two or more drag electrodes to translocate the linear charged polymer by one or more monomers.

17. The method of claim 5, wherein the three locking electrodes comprise a first locking electrode and a second locking electrode, such that the one or more characterization activities comprise measuring tunnel current between the first locking electrode and the second locking electrode.

18. The method of claim 5, wherein the three locking electrodes comprise a first locking electrode and a second locking electrode, such that the one or more characterization activities comprise measuring capacitance change between the first locking electrode and the second locking electrode.

19. The method of claim 7, wherein the step of increasing the time-dependent voltage to each of the two or more drag electrodes comprises increasing the time-dependent voltage to each of the two or more drag electrodes for a time interval, wherein the time interval is sufficient to translocate each polymer by one monomer.

20. The method of claim 7, wherein the step of increasing the time-dependent voltage to each of the two or more drag electrodes to translocate the linear charged polymer by one or more monomers comprises translocating the linear charged polymer in both directions.

* * * * *